United States Patent [19]
Huber et al.

[11] Patent Number: 6,040,145
[45] Date of Patent: Mar. 21, 2000

[54] POTENTIATION OF THE IMMUNE RESPONSE

[75] Inventors: Brigitte T. Huber, Boston; Tracy Schmitz, Cambridge; Robert Underwood, Quincy, all of Mass.

[73] Assignee: Tufts University, Boston, Mass.

[21] Appl. No.: 08/852,395

[22] Filed: May 7, 1997

[51] Int. Cl.$^7$ .................. G01N 33/53; G01N 33/567; A61K 38/48
[52] U.S. Cl. .................. 435/7.2; 435/7.71; 435/7.72; 424/94.64
[58] Field of Search .................. 435/7.2, 7.71, 435/7.72; 424/94.64

[56] References Cited

U.S. PATENT DOCUMENTS 5,329,028  7/1994  Ashkenzi et al. .

FOREIGN PATENT DOCUMENTS

WO91/17767  11/1991  WIPO .
9403055  2/1994  WIPO .
WO94/25873  11/1994  WIPO .
WO95/29691  11/1995  WIPO .

OTHER PUBLICATIONS

Schmitz, et al, "Potentiation of the immune response . . . " J. Clin. Invest. 97(6): 1545–1549, 1996.
Kubota, et al, "Involvement of dipeptidyl . . . " Clin. Exp. Immunol. 89: 192–197, 1992.
Flentke, et al, "Inhibition of dipeptidyl amino–peptidase . . . " PNAS 88: 1556–1559, 1991.
Markowitz, et al. : A preliminary study if ritonavir . . . : N.E.J.M.: vol. 333, No. 23:pp. 1534–1539, Dec. 1995.
Wijdenes et al., "Monoclonal Antibodies (mAb) against gp130 Imitating Cytokines Which Use the gp130 for Signal Transduction", (Jul. 1995), p. 303.
Blumenstein et al., Biochem. Biophys. Res. Comm. 163:980–987.
"Update on Viral Pathogenesis," by Ronald B. Luftig, ASM News 56:368, 1990.
"Inhibition of Human Immunodeficiency Virus Type 1 Infection in a T–Cell Line (CEM) by new Dipeptidyl–Peptidase IV (CD26) Inhibitors," J.D. Jiang et al., Res. Virol., 1997, 148, pp. 255–266.
"Structure–Activity Relationships of Boronic Acid Inhibitors of Dipeptidyl Peptidase IV. 1. Variation of the $P_2$ Position of $X_{aa}$–boroPro Dipeptides," Simon J. Coutts et al., J. Med. Chem. 1996, 39, pp. 2087–2094.
"Generation and Use of Nonsupport–Bound Peptide and Peptidomimetic Combinatorial Libraries," J.M. Ostresh et al., Methods in Enzymology, vol. 267, Chapter 13, edited by John N. Abelson, 1996, Academic Press, San Diego, ISBN 0–12–182168–4.

Primary Examiner—Jeffrey Stucker
Assistant Examiner—Brett Nelson
Attorney, Agent, or Firm—Ivor R. Elrifi; Mintz Levin

[57] ABSTRACT

A method for stimulating proliferation of T-cells containing cytoplasmic post-prolyl dipeptidase activity; the method, in one aspect, involves contacting the T-cells with an organic compound at a concentration below $10^{-8}$M, wherein the compound is characterized in that: (a) it is capable of crossing the membrane of T-cells to enter the cytoplasm, (b) it binds to the dipeptidase activity at a concentration of below $10^{-8}$M, and thus (c) stimulates proliferation of the T-cells at that concentration.

7 Claims, 7 Drawing Sheets

POTENTIATION OF THE IMMUNE RESPONSE

STATEMENT AS TO FEDERALLY SPONSORED RESEARCH

This invention was made with Government support under NIH grant No. AI36696, and the Government therefore has certain rights in this invention.

BACKGROUND OF THE INVENTION

This invention relates to treatment of viral infections using organic compounds which interact with T-cell enzymes.

One of the classic markers of full-blown AIDS resulting from long-term infection with HIV-1 is a severe depletion of $CD4^+$ T-cells, which are a key component of the immune system. Attempts have been made to increase the $CD4^+$ counts of AIDS patients, and some of these efforts, notably treatment with protease inhibitors, have met with considerable success. Other approaches, e.g., stimulation of the immune response by vaccination with viral peptides, have been less successful. The reasons for $CD4^+$ depletion in AIDS, and resistance of $CD4^+$ cells to stimulation by some therapies, are not fully understood.

SUMMARY OF THE INVENTION

We have discovered that the activation state of human T-cells can be affected by compounds which interact with a cytoplasmic post-prolyl dipeptidase activity which has similarities to, but is distinct from, the membrane-bound T-cell serine protease CD26. The compounds useful in the invention are inhibitors of this activity, which is, in naturally-occurring T-cells in healthy individuals, involved in protection of T-cells from apoptosis, or programmed cell death. Thus, in high concentrations, the inhibitors hasten the death of T-cells, by inhibiting the protective enyzme. We have discovered, surprisingly, that at low concentrations the inhibitors exhibit a paradoxical effect: they are potent stimulators of T-cell activity in HIV-infected individuals. The concentrations of inhibitor which induce this T-cell stimulatory response are very low (on the order of $10^{-8}$–$10^{-12}$M), and therefore the inhibitors can be used with minimal side effects, even if, in larger doses, the inhibitors would be toxic.

Our hypothesis is that the resistance to full activation observed in T-cells of HIV-infected individuals involves a blocking of the cytoplasmic enzymatic activity discussed above. We believe that this blocking of activation, involving this cytoplasmic activity, prevents differentiation of T-cells of HIV-infected individuals into effector cells, eventually leading to T-cell death.

Thus, the invention features a method for stimulating proliferation of T-cells of a human patient suffering from a disease state characterized by the inability of the patients' T-cells to respond normally to T-cell proliferation-inducing stimuli; the method involves contacting the T-cells with an organic compound at a concentration below $10^{-8}$M, wherein the compound is characterized in that it binds to the post-prolyl cleaving dipeptidase activity present in the cytoplasm of human T-cells, e.g., $CD4^+$ cells or Jurkat cells.

Treatment according to the invention can be in vitro or in vivo. In in vivo therapy, the enzyme-interacting compound of the invention is administered such that the blood concentration in the patient (e.g., an HIV-infected patient) is below $10^{-11}$. The compounds can also be used in vitro at low concentrations to stimulate proliferation of non-infected, beneficial T-cells, such as $CD4^+$ cells and CTL's. In this embodiment, PBMC are isolated from a patient and incubated with a concentration of lower than $10^{-8}$M of the compound, to bring about proliferation of T-cells, which are then reinfused into the patient.

We believe that administration of low concentrations of the inhibitors of the invention may have an allosteric effect such that the T-cell cytoplasmic enzyme, which is a multimeric (i.e., multiple subunit) enzyme, exhibits an increased affinity of the enzyme for its natural substrate or ligands, allowing the previously blocked T-cell to proceed to full activation, and hence survival, proliferation, and interleukin-2 production. Stimulation of the T-cell immune response in HIV-infected patients according to the invention yields increased numbers of immune effector cells, which can fight both HIV itself, and other opportunistic pathogens.

Treatment according to the invention has the advantages of specificity and low toxicity, not just because of the low concentrations of inhibitor which can be used, but also because, in T-cells of patients not infected with a virus such as HIV, the inhibitors have no discernable effect. Furthermore, treatment according to the invention advantageously does not necessarily require in vitro manipulation of the T-cells from HIV-infected patients. Furthermore, no immunization is required, and treatment will be effective even where HIV proteins have mutated because the therapy targets a cellular enzyme. The fact that, in T-cells treated according to the invention in vitro, no increase in the level of the HIV protein p24 is observed, probably indicates that the T-cells which are infected with HIV are not stimulated by the low dose inhibitor treatment of the invention.

The invention also permits immunization of HIV-infected patients with, e.g., HIV peptides. Under normal circumstances, such patients cannot be vaccinated because of the defect in the T-cell stimulation pathway. Use of inhibitors in low doses as adjuvants can render T-cells responsive to vaccination with HIV antigens, in particular peptides.

Treatment of HIV-infected patients with low doses of inhibitors according to the invention can also enhance the activity of other AIDS drugs, in particular protease inhibitors. We have found that treatment according to the invention generally fails to bring about an increase in $CD4^+$ count in patients whose $CD4^+$ count is already very low, i.e., below about 400. In such patients, the $CD4^+$ count can be increased to above this level using known protease inhibitors, and the newly generated $CD4^+$ T-cells resulting from such treatment are particularly susceptible to the stimulatory effects of treatment according to the invention, leading to an optimal combination AIDS therapy. Preferably, the drugs are administered orally.

The low dose administration of inhibitors of the invention can also be used to produce an adjuvant effect in HIV-negative individuals, who are to be immunized with peptides or other viral antigens; this mode of vaccination can be used for prophylaxis for HIV, as well as any other viral pathogen. Ordinarily, meaningful cytolytic T-lymphocyte ("CTL") responses, both in vitro and in vivo, have been difficult to achieve with peptide immunization. The invention should make it possible to produce significant CTL responses to viral peptides, e.g., peptides from influenza, HIV, human papilloma virus, and herpes peptides. This adjuvant effect can also be used to stimulate CTL responses to peptide antigens from other pathogens as well, e.g., pathogenic bacteria such as toxigenic *E. coli,* and protozoan pathogens such as the pathogens which are the causative agents of malaria and amoebic dysentery. The compounds, when used as adjuvants, are preferably administered orally.

The invention provides a new and highly advantageous method of potentiating the immune response in both HIV infected and uninfected patients, in methods employing extremely low concentrations of inhibitors which, at these concentrations, exhibit a paradoxical effect (i.e., they act as stimulatory rather than inhibitory molecules, as they would at higher concentrations). The very low concentrations employed according to the invention allows treatment with minimal side reactions and toxicity. The specificity of the treatment of the invention also avoids such adverse effects, which are seen, for example, in treatment with immune stimulatory compounds such as interleukin-2.

Other features and advantages of the invention will be apparent from the following detailed description thereof and from the claims.

BRIEF DESCRIPTION OF THE DRAWINGS

FIG. 1A shows the effect of the compound on T-cell proliferation in vitro for PBMC from an HIV-1$^+$ individual and FIG. 1B shows the effect of the compound on T-cell proliferation in vitro on PBMC from an HIV-1$^-$ individual. Each of FIGS. 1A and 1B illustrate a representative experiment out of a total of ten experiments.

DETAILED DESCRIPTION

Therapeutic Compounds

Figure 1A:
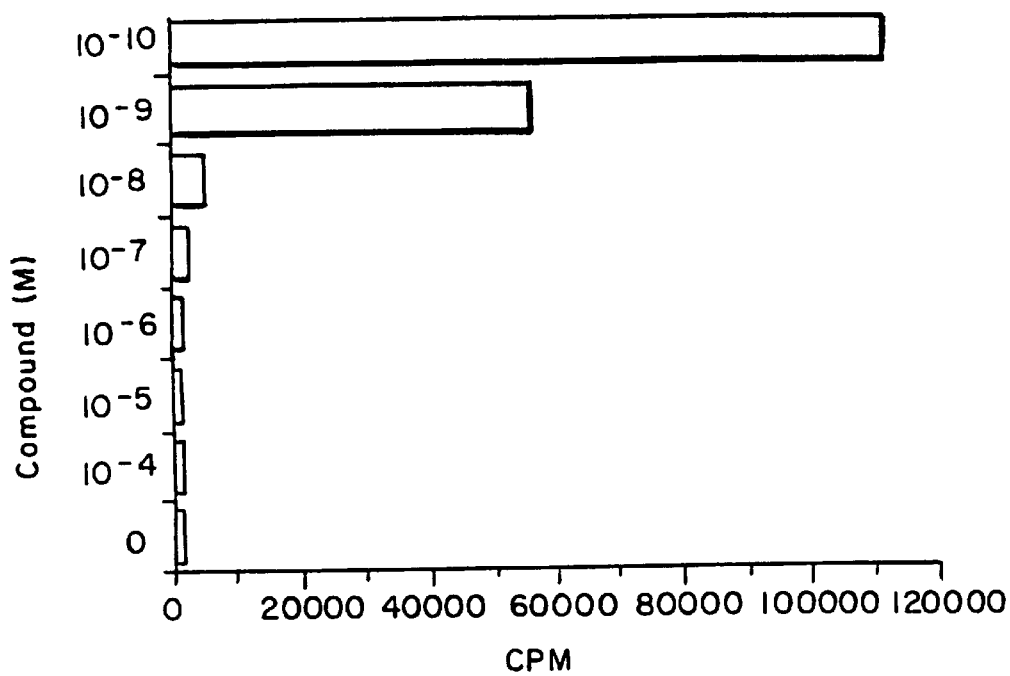
FIGS. 1A and B are a pair of graphs showing the lymphocyte stimulatory effect of treatment of the invention on peripheral blood mononuclear cells (PBMC) from HIV-infected and uninfected patients.

Any organic compound can be used according to the invention which exhibits the following properties: (1) it is capable of crossing the membrane of human T-cells to reach the cytoplasm, where the compound can (2) interact with the cytoplasmic dipeptidase present in the T-cells, in order to (3) stimulate activation/proliferation of T-cells (and most preferably CD4$^+$ cells or CTLs) at concentrations below 10$^{-8}$M.

A simple screening method is described below for the identification of compounds which are candidate therapeutic compounds according to the invention.

Substrate and Enzyme Preparation

The first step is to provide a cytoplasmic enzyme preparation. The preparation need not be a pure enzyme sample; a crude cytoplasmic extract is sufficient to screen compounds for the desired activity. The extract can be prepared from any human T-cell line which is negative for CD26; an example of such a suitable cell line is the commercially available Jurkat cell line.

A suitable enzyme-containing cell extract can be prepared as follows. First, Jurkat cells (10$^6$–10$^{11}$ cells) are grown and a cell pellet is obtained by centrifugation. The cell pellet is stored in frozen condition.

For use in the assay, the frozen pellet is thawed by the addition of ice cold lysis buffer, in the amount of approximately 1 ml per 10$^8$ cells. The liquified material is homogenized with ten strokes of a Dounce homogenizer, and then clarified by centrifugation at 1500 g. The supernatant is removed (and saved), and the 1500 g. pellet is resuspended in lysis buffer and homogenized with ten strokes of a Dounce homogenizer. Clarification is again carried out by centrifugation at 1500 g, 4° C.

The 1500 g supernatants are then combined, and EDTA is added to 5 mM. The resultant liquid is centrifuged at 75,000 g at 4° C. for twenty minutes, and the supernatant is then removed and centrifuged at 175,000 g. at 4° C., for 60 minutes. The resultant supernatant, containing the cytosolic extract, is the DPPV activity-containing preparation used in the assay, described below, for candidate therapeutic compounds of the invention.

The assay is based on our observation that the T-cell cytoplasmic enzyme of interest is a post-prolyl cleaving serine protease. We therefore chose as a reporter substrate a compound which contains proline in the penultimate position; any of a number of substrates meeting this requirement can be used. In the assay described herein, we employed a fluorescent cleavage assay using the substrate AlaProAFC. Alternatively, a colorimetric assay can be carried out using as a substrate Gly-Pro-pNA. The choice of terminal amino acid is not critical, provided that the substrate contain a free terminal amino group.

In the assay we carried out, we employed a fluorescence spectrometer for excitation at 400 nm and emission at 505 nm. The spectrometer was calibrated for fluorescence intensity of 0.000=10 mM HEPES, pH 7.4; and fluorescence intensity of 1.000=10 Mm HEPES, 1 μM AFC.

To carry out the assay, between 10 and 100 μl of enzyme extract, above, is diluted to 1 ml with 10 mM HEPES, pH 7.4, containing 10 mM Ala-Pro-AFC. At least one extract/substrate sample is run without test compound, to provide a standard for comparison with the test sample.

In the test samples, multiple samples are run containing varying concentrations, down to $10^{-8}M$, of the test compound. The sample (with or without test compound) is placed in a cuvette, and inserted into a fluoresent spectrometer. Enzymatic activity is measured as the accumulation of fluoresence intensity (i.e., substrate cleavage product) over time (1 min.). A compound is identified as an inhibitor if the accumulative fluoresence is decreased as a result of the presence of the inhibiting compound.

Once a compound has been identified as an enzymatic inhibitor, as described above, further assays are carried out to determine whether the compound is capable of moving across the T-cell membrane into the cytoplasm; this is an assay which can be carried out using well-known techniques.

Figure 4:
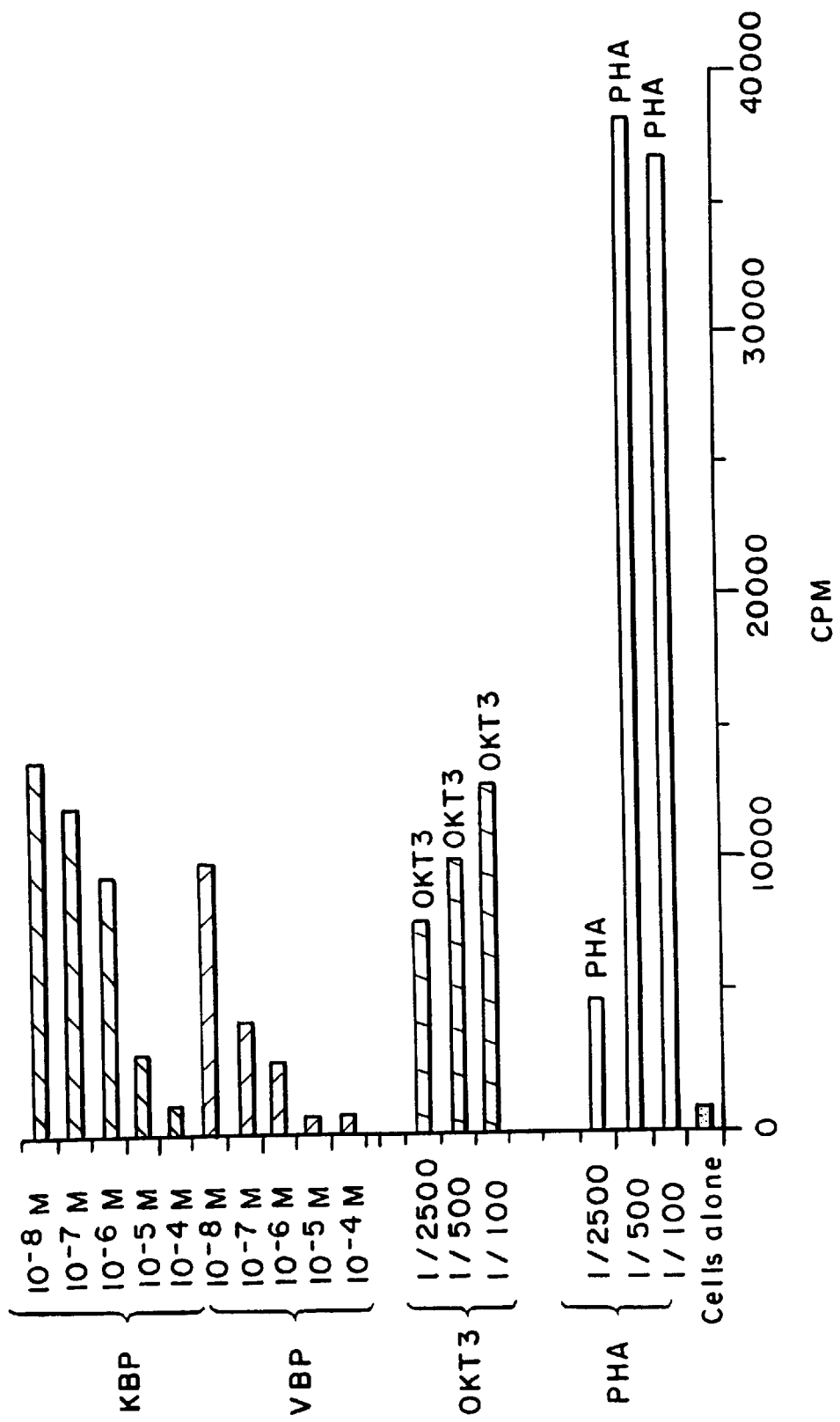
FIG. 4 is a graph showing the stimulatory effect of treatment according to the invention in lymphocytes of HIV-infected patients, compared to treatment using two control compounds (date of experiment Mar. 23, 1995; patient id no. 1586496; CD4 antibody count: 830; number of cells/well: 0.4×10$^6$).

If desired, additional in vitro assays can be carried out using candidate compounds of the invention, prior to their use in vivo. One such assay employs the candidate compound at a very low concentration, in a test designed to determine whether at low concentrations the compound can stimulate the proliferation of PBMC from HIV infected patients in vitro. As is shown in the data of FIG. 4, stimulation can be measured by, e.g., incorporation of a labelled nucleotide.

Figure 6:
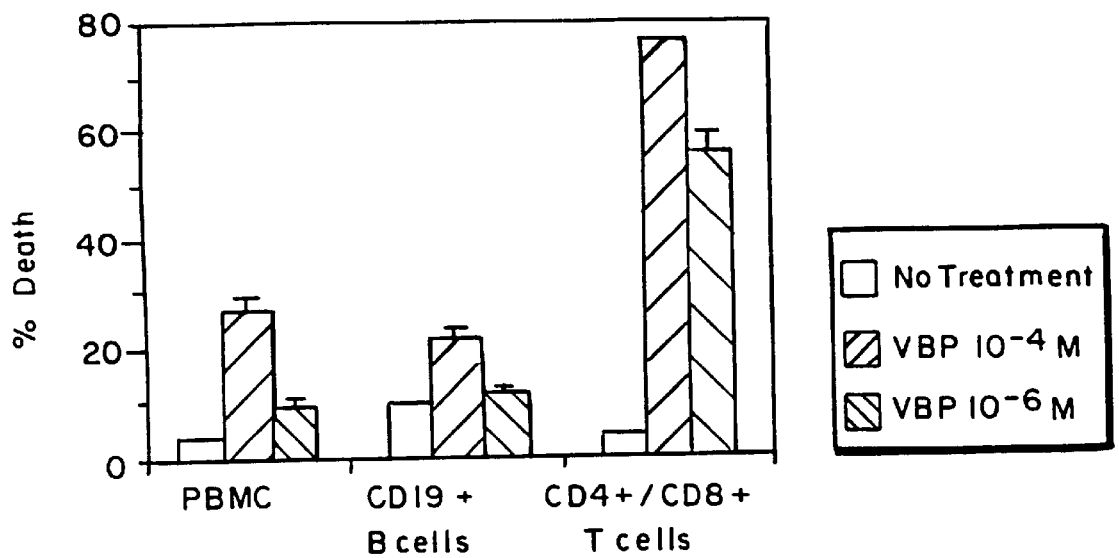
FIG. 6 is a histogram demonstrating that an inhibitor according to the invention induces dose-dependent apoptosis in resting T-cells (these dosages are higher than the extremely low doses used according to the invention). CD19+B cells and CD4+/CD8+Tells were isolated (>90% and >97% purity, respectively). The cells were then incubated overnight in the presence or absence of VBP (10$^{-4}$ M or 10$^{-6}$ M). The amount of death induced by VBP treatment was determined by 7AAD flow cytometry analysis. The data represents the mean percent of death from duplicate samples.

The compounds can also be tested at higher doses to determine whether they exhibit the opposite effect of proliferation, as above, i.e., dose-dependent apoptosis caused by enzyme inhibition, as in the experiments of FIG. 6.

Candidate Compounds

As is discussed above, compounds which are potentially capable of apoptosis induction at high doses and proliferation induction at low doses are those which, at normal or high doses, inhibit cytoplasmic T-cell dipeptidase, and can cross the T-cell membrane into the T-cell cytoplasm, where the enzyme interaction occurs. The compounds thus should be organic compounds which have a free amino group at the amino terminus; a proline or proline analog at the penultimate position; and an enzyme binding site which mimics the post-prolyl cleavage site of cytoplasmic dipeptidase.

A number of known classes of compounds can be screened and used according to the invention. Once such class are CD26 (i.e., DPPIV) inhibitors, including those described in Bachovchin et al. U.S. Pat. No. 4,935,493, hereby incorporated by reference. In the '493 patent, there are described compounds having the structure:

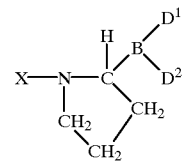

where each D1 and D2, independently, is a hydroxyl group or a group which is capable of being hydrolyzed to a hydroxyl group in aqueous solution at physiological pH; and X comprises an amino acid or a peptide which mimics the site of the substrate recognized by a post-prolyl cleaving enzyme.

The compounds in the '493 patent are inhibitors of CD26, and are also candidate inhibitors of the invention. As is discussed above, because of the low concentrations of compounds used according to the invention, it is acceptable to use, in the invention, a compound which interacts not only with the cytoplasmic enzyme, but also CD26.

The class of compounds described in the '493 patent are also discussed and exemplified in Takacs et al. U.S. patent application Ser. No. 07/923,337, corresponding to PCT Application No. WO94/03055, hereby incorporated by reference. In this application, one of the families of molecules in the '493 patent is described as the "Xaa-boroPro molecules," exemplified by Ala-boroPro, Pro-boroPro, and Gly-boroPro. These Xaa-boroPro molecules are all candidate compounds for use in the methods of the present invention. Two of these compounds are used in some of the examples described below; those compounds are Lys-boroPro ("KPB"), and Val-boroPro ("VBP").

EXAMPLE 1

Peripheral blood mononuclear cells (PBMC) were obtained by standard methods from HIV-infected individuals, and from uninfected individuals. Varying dosages of KBP or VBP were contacted with the PBMC in vitro, and stimulation of proliferation was measured by incorporation of $^3H$ thymidine (cpm). The results of these experiments are shown in FIG. 1: very low doses of the Val-boroPro and Lys-boroPro stimulated proliferation of PBMC from HIV-infected patients, but not PBMC from uninfected patients.

Figure 1B:
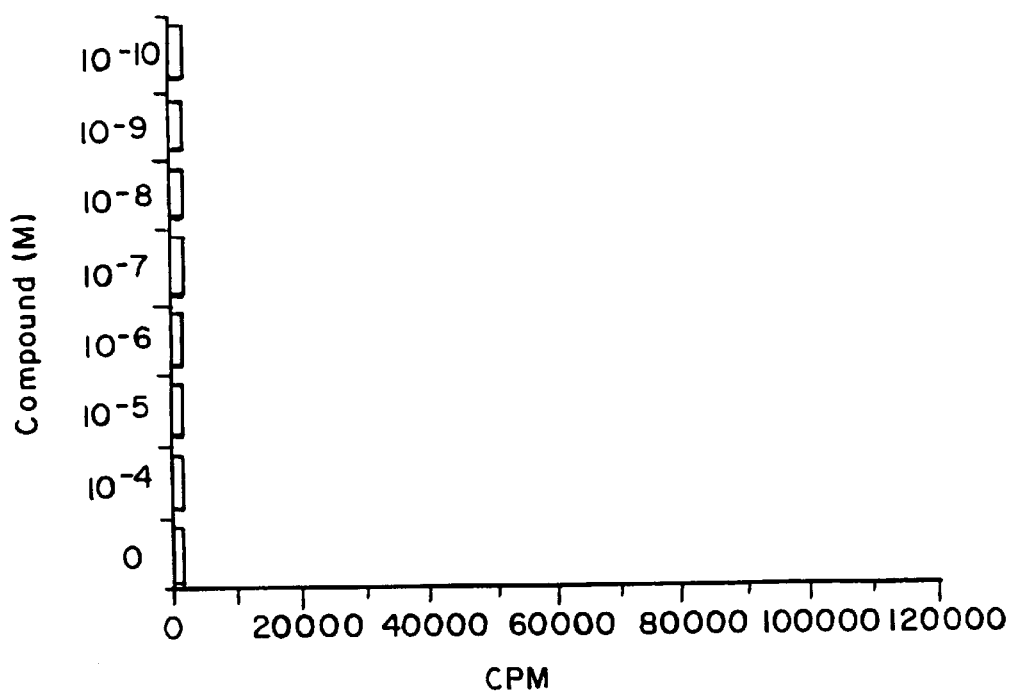

As shown in FIG. 1, at no concentration of the boroPro enzyme inhibitor did it affect the PBMC from uninfected individuals. The inhibitor, at moderate concentrations, also did not cause proliferation of PBMC from HIV-infected individuals, but it did cause marked proliferation at very low concentrations ($10^{-9}$ and $10^{-10}$). These results are consistent with our hypothesis, discussed above, that, at low concentrations, these enzyme inhibitors exhibit a paradoxical effect: rather than inhibiting the apoptosis-controlling cytoplasmic T-cell enzyme, they interact with that enzyme in a manner which blocks inactivation and causes proliferation of T-cells.

Figure 2:
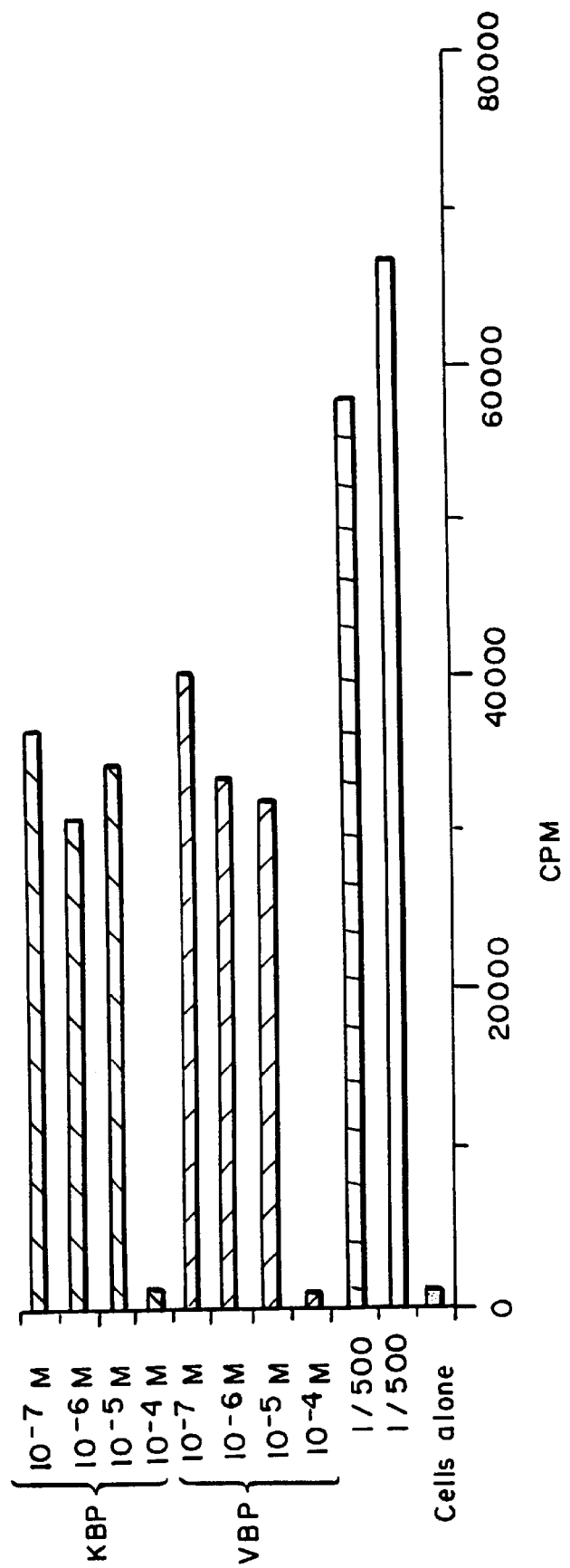
FIG. 2 is a graph illustrating the T-cell stimulatory effects of two inhibitory compounds used according to the invention (date of experiment: Mar. 9, 1995; patient id no:1655185; CD4 antibody count:760; and number of cells/well: 0.4×10$^6$).

Concordant results are shown in FIG. 2, a histogram showing that low doses of Lys-boroPro and Val-boroPro cause proliferation of PBMC of HIV-infected patients, while higher doses ($10^{-4}M$) do not have this effect.

Figure 3:
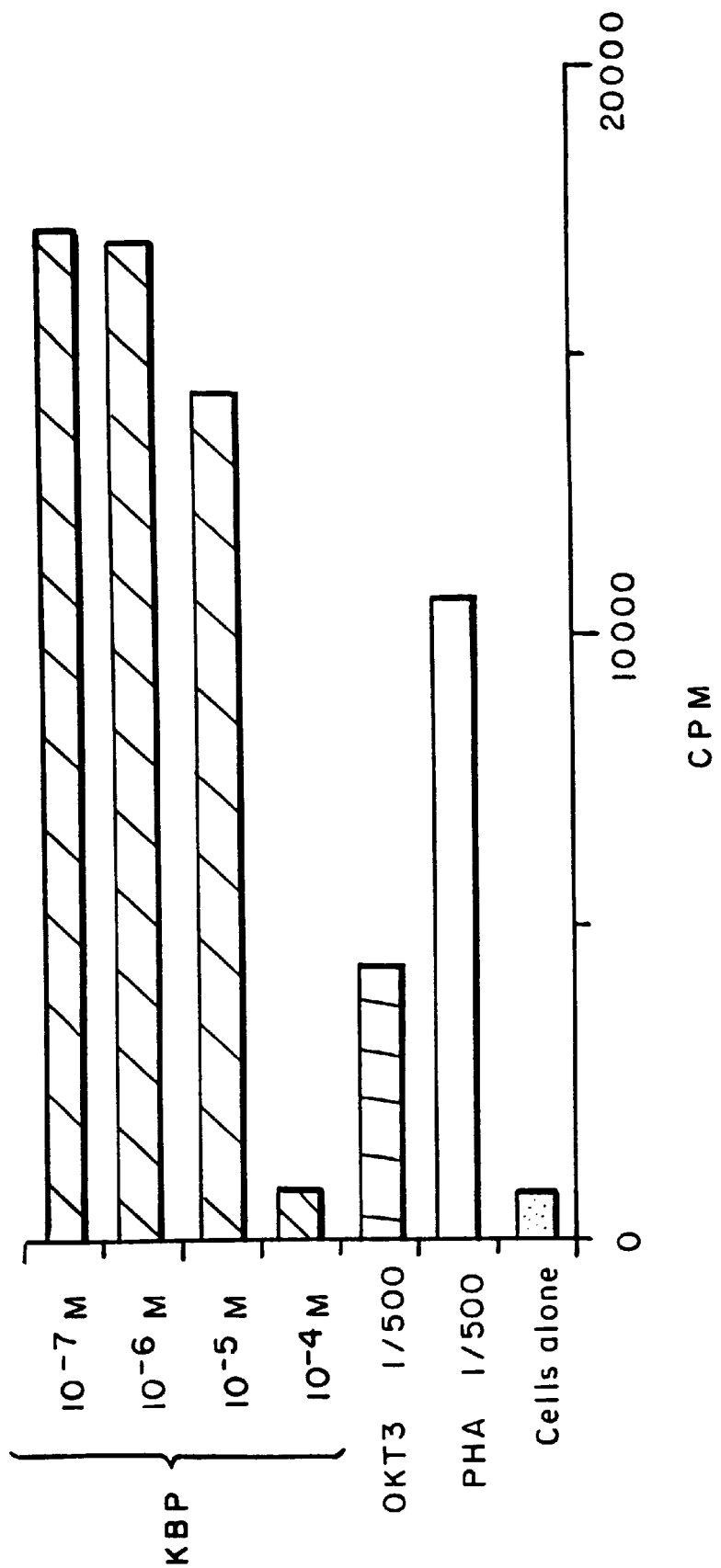
FIG. 3 is a graph showing the stimulatory effect of treatment according to the invention in lymphocytes of HIV-infected patients, compared to treatment using two control compounds (date of experiment: Mar. 15, 1995; patient id no: 1227604; CD4 antibody count: 230; number of cells/well: 0.16×10$^6$; and ½ area of a 96 well plate).

The same results are shown in FIGS. 3 and 4 which also present data for two control compounds OKT3, and PHA, both of which are non-specific mitogens.

Figure 5:
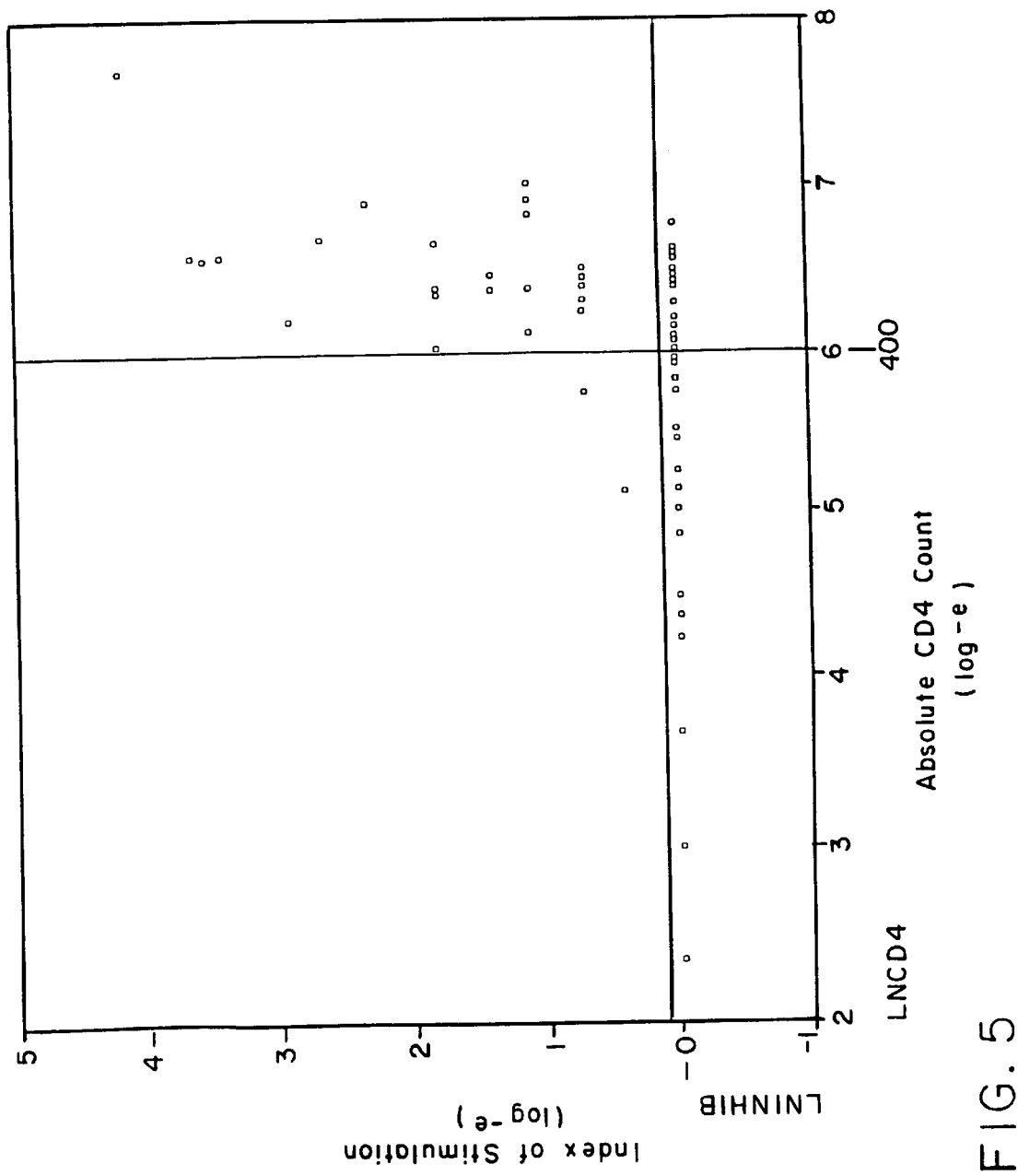
FIG. 5 is a graph illustrating a stimulatory effect of an inhibitor according to the invention on PBMC in vitro, showing the correlation with CD4$^+$ counts. The data are plotted as the natural log of the stimulation index (vertical dimension) versus the natural log of the CD4$^+$ count of the patient (horizontal dimension)(71 patients total; P=<0.0001; RR=2.04 (1.5–2.9)).

Referring to FIG. 5, data are presented in a form which shows that low concentrations of the inhibitors of the invention have little effect on the PBM C of HIV-infected patients whose CD4 counts are lower than about 400 (the clinical indication for AIDS). In the graph of FIG. 5, the natural log of the stimulation index (the vertical axis) is plotted against the natural log of the CD4 count of the patients; as shown, above a count of 400 there is particularly significant stimulation of proliferation.

FIG. 6 is a graph demonstrating that purified T-cells are highly sensitive to cytoplasmic T-cell dipeptidase inhibitors in moderate concentrations. CD 19$^-$ B cells and CD4$^+$/CD8$^+$ T-cells were isolated to high purity and incubated overnight in Val-boroPro. The amount of cell death was determined by 7AAD flow cytometry analysis. Data represent % of cell death from duplicate samples. These data are consistent with our hypothesis that the inhibitors, in moderate concentration, inhibit a cytoplasmic enzyme which ordinarily protects against apoptosis.

Figure 7:
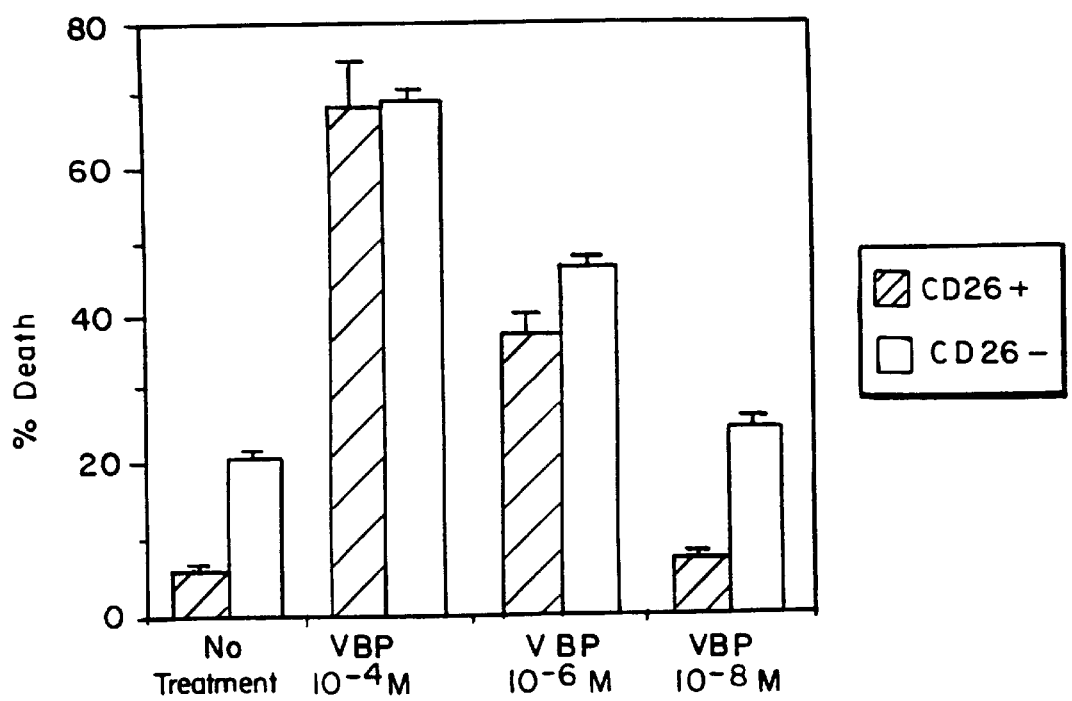
FIG. 7 is a histogram demonstrating that an inhibitor according to the invention induces, at higher doses than in the invention, dose-dependent apoptosis in both CD26$^-$ and CD26$^-$ populations of PBMC. The CD26$^+$ and CD26$^-$ PBMC populations were found to be equally susceptible to DPPIV inhibitor induced death. PBMC were stained with the anti-CD26 monoclonal antibody, 4 EL, and then sorted into CD26$^+$ and CD26$^-$ populations using a facstar plus dual lasar flow cytometry. The cells expressing the highest level (top 5%) of CD26 and the cells expressing the lowest level (bottom 10%) of CD26 were isolated as the CD26$^+$ and CD26$^-$ populations respectively. The purity of the populations as examined by staining with the anti-CD26 monoclonal antibody, 134-2C2, is >90%. The CD26$^+$ and CD26$^-$ populations were cultured overnight in the presence or absence of various concentrations of VBP. The amount of death induced by VBP treatment was determined by 7AAD flow cytometry analysis. Data represent mean percent of death from duplicate samples +/−SD.

FIG. 7 presents data demonstrating that CD26$^+$ and CD26$^-$ PBMC are equally susceptible to T-cell cytoplasmic enzyme inhibitor-induced death, where the inhibitor is administered in moderate concentrations. CD26$^-$ and CD26$^-$ populations were incubated overnight in the presence or absence of various concentrations of Val-boroPro. The amount of cell death was determined by 7AAD flow cytometry analysis. Data represent mean % of death from duplicate samples. These data indicate that apoptosis-inhibiting T-cell cytoplasmic enzyme is present in both CD26$^-$ and CD26$^-$ T-cells.

Figure 8:
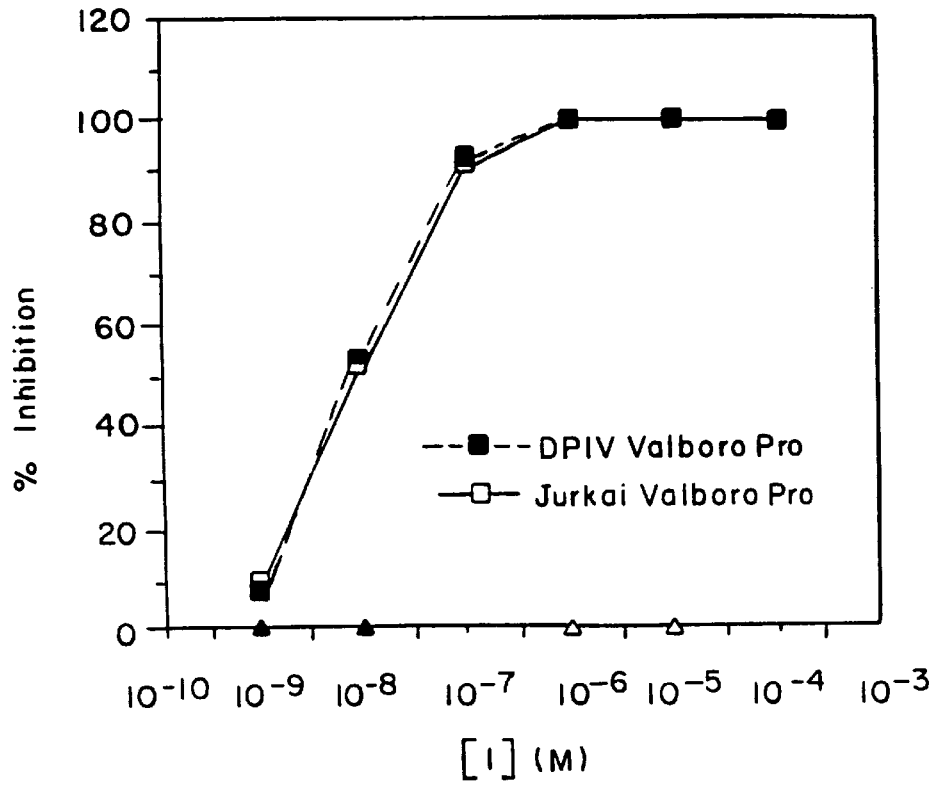
FIG. 8 is a graph showing that an inhibitor of CD26 (val-boroPro) inhibited the cytoplasmic enzyme as well.
Figure 9:
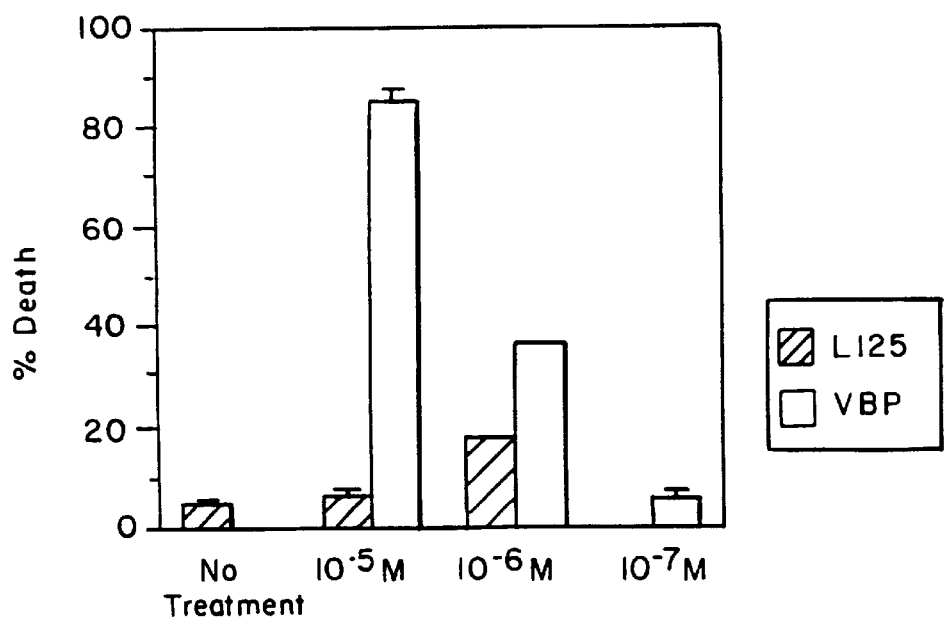
FIG. 9 is a graph showing the stimulatory effect of treatment according to the invention in lymphocytes of HIV-infected patients, compared to treatment using two control compounds. Fluoroolefins did not induce cell death. PBMC were cultured overnight in the presence or absence of DPPIV inhibitors, L125, a fluoroolefin containing N-peptidyl-O-acylhydroxylamines inhibitor or VBP. The amount of death induced was determined by 7AAD flow cytometry analysis. The data represents the mean percent death from duplicate samples.

FIG. 8 presents data showing the effects of an inhibitor useful in the invention, Val-boroPro. The experiments were carried out using two preparations: purified DPPIV (i.e., CD26), and Jurkat T-cell cytoplasmic extract, described above (Jurkat cells contain the cytoplasmic T-cell enzyme, but do not bear CD26 on their surfaces). These preparations were incubated with varying concentrations of Val-boroPro, and enzymatic activity was determined by measuring the accumulation of the fluorescent cleavage product 7-amino-4-trifluoromethylcoumarin (AFC) released from the substrate Ala-ProAFC upon enzymatic cleavage. Val-boroPro inhibited both the enzyme DPPIV and the cytoplasmic T-cell enzyme in the Jurkat preparation.

Other embodiments are within the following claims.

What is claimed is:

1. A method for stimulating proliferation of T-cells of a human patient; said method comprising contacting said T-cells, in vitro, with an organic compound having the structure:

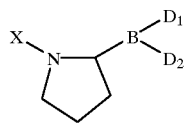

wherein B is boron, each D1 and D2 independently, is a hydroxyl group or a group which is capable of being hydrolyzed to a hydroxyl group in aqueous solution at physiological pH; and X comprises an amino acid or a peptide which mimics the site of a substrate recognized by a post-prolyl cleaving enzyme; at an in vitro concentration below 10$^{-8}$M, wherein said compound inhibits the post-prolyl cleaving dipeptidase activity present in the cytoplasm of Jurkat cells and said patient suffers from a disease state caused by HIV infection.

2. The method of claim 1 wherein said compound at a concentration of 10$^{-8}$ M, binds to the cytoplasmic post-prolyl cleaving dipeptidase activity of CD4$^+$ T-cells of HIV-infected patients, to stimulate proliferation of said cells.

3. The method of claim 1, wherein said compound is a serine protease inhibitor.

4. The method of claim 3, wherein said serine protease inhibitor has a cleavage site or a binding site which mimics a post-proline serine protease cleavage site.

5. A method for stimulating proliferation of T-cells which contain cytoplasmic post-prolyl cleaving dipeptidase activity and which are further characterized by the inability to respond normally to T-cell proliferation-inducing stimuli, said method comprising contacting said T-cells in vitro with an organic compound at a concentration below 10$^{-8}$M, wherein said compound has the following structure:

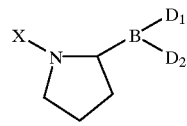

wherein B is Boron) each D1 and D2 independently, is a hydroxyl group or a group which is capable of being hydrolyzed to a hydroxyl group in aqueous solution at physiological pH; and X comprises an amino acid or a peptide which mimics the site of a substrate recognized by a post-prolyl cleaving enzyme, and said compound: (a) crosses the membrane of said T-cells to enter the cytoplasm, (b) inhibits said dipeptidase activity at a concentration below 10$^{-8}$M, and thus (c) stimulates proliferation of said T-cells at said concentration.

6. The method of claim 5, wherein said T-cells are CD4+ T-cells.

7. The method of claim 6, wherein said compound enhances the ability of said CD4$^+$ T-cells to proliferation in response to antigenic stimulation.

* * * * *

UNITED STATES PATENT AND TRADEMARK OFFICE
CERTIFICATE OF CORRECTION

PATENT NO. : 6,040,145  
DATED : March 21, 2000  
INVENTOR(S) : Huber, B. et al.

Page 1 of 1

It is certified that error appears in the above-identified patent and that said Letters Patent is hereby corrected as shown below:

<u>Column 8,</u>  
Line 1, delete "independently," and replace with -- independently --;  
Line 39, delete "Boron)" and replace with -- Boron, --;  
Line 39, delete "independently," and replace with -- independently --;  
Line 54, delete "proliferation", and replace with -- proliferate --.

Signed and Sealed this

Twenty-fifth Day of April, 2006

JON W. DUDAS  
*Director of the United States Patent and Trademark Office*